US00PP22125P2

(12) United States Plant Patent
van Kleinwee

(10) Patent No.: US PP22,125 P2
(45) Date of Patent: Sep. 6, 2011

(54) *PELARGONIUM* PLANT NAMED 'ZOPFLAIR'

(50) Latin Name: *Pelargonium peltatum*
Varietal Denomination: Zopflair

(75) Inventor: Theodorus Cornelis Maria van Kleinwee, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/799,831

(22) Filed: May 3, 2010

(51) Int. Cl.
*A01H 5/00* (2006.01)

(52) U.S. Cl. ..... Plt./328

(58) Field of Classification Search ..... Plt./328, Plt./325, 329, 332
See application file for complete search history.

*Primary Examiner* — Susan McCormick Ewoldt
(74) *Attorney, Agent, or Firm* — S. Matthew Edwards

(57) ABSTRACT

A new *Pelargonium* plant named 'Zopflair' particularly distinguished by the relatively large, double red-purple flowers, umbels held well above the foliage, having early to mid season flowering with medium green foliage with distinct zonation, and initially semi-upright, then semi-trailing well-branched plant habit.

1 Drawing Sheet

Latin name of the genus and species of the plant claimed: *Pelargonium peltatum.*

Varietal denomination: 'Zopflair'.

BACKGROUND OF THE NEW PLANT

The present invention comprises a new *Pelargonium*, botanically known as *Pelargonium peltatum*, and hereinafter referred to by the variety name 'Zopflair'.

'Zopflair' is a product of a planned breeding program. The new cultivar has relatively large, double red-purple flowers, umbels held well above the foliage, having early to mid season flowering with medium green foliage with distinct zonation, and initially semi-upright then semi-trailing well-branched plant habit.

'Zopflair' originated from a hybridization made in May 2004 in a controlled breeding environment in Enkhuizen, Netherlands. The female parent was the commercial variety named 'Sil Teske', unpatented, having light lavender colored flowers, foliage with weak zonation and a medium to tall plant habit.

The male parent of 'Zopflair' was 'Free Cherry Rose', U.S. Plant Pat. No. 12,448 with double magenta colored flowers, foliage without zonation, and relatively small plant habit.

The resulting seeds were sown in December 2004 and 'Zopflair' was selected as one flowering plant within the progeny of the stated cross in May 2005 in a controlled environment in Enkhuizen, Netherlands.

The first act of asexual reproduction of 'Zopflair' was accomplished when vegetative cuttings were propagated from the initial selection in September 2005 in a controlled environment in Enkhuizen, Netherlands.

BRIEF SUMMARY OF INVENTION

Horticultural examination of plants grown from cuttings of the plant initiated in Enkhuizen, Netherlands, and continuing thereafter, has demonstrated that the combination of characteristics as herein disclosed for 'Zopflair' are firmly fixed and are retained through successive generations of asexual reproduction.

'Zopflair' has not been observed under all possible environmental conditions. The phenotype may vary significantly with variations in environment such as temperature, light intensity and day length.

Plant Breeder's Rights for this cultivar have been applied for in Switzerland on Jul. 6, 2009 (#09-2602), in Canada on Oct. 30, 2009 (#09-6780), and in CVPO on Feb. 25, 2010 (#2010-0456). 'Zopflair' has not been made publicly available more than one year prior to the filing of this application.

The following traits have been repeatedly observed and are determined to be basic characteristics of the new variety. The combination of these characteristics distinguishes this *Pelargonium* as a new and distinct variety.

BRIEF DESCRIPTION OF THE PHOTOGRAPHS

The accompanying photographic drawings show typical flower and foliage characteristics of 'Zopflair' with colors being as true as possible with an illustration of this type. The photographic drawing shows a flowering potted plant of the new variety, and a close-up of the flowers in the inset. The plant was grown in Hillscheid, Germany and was about 6 to 7 months of age. The photo was taken in June 2009 in Hillscheid, Germany.

DETAILED BOTANICAL DESCRIPTION

The measurements were taken in Hillscheid, Germany in late April 2009 on 12 week old plants that were growing in a greenhouse. Cultivation of these plants started in early February 2009, when rooted cuttings were planted into 12 cm pots, were terminally-pinched once in mid February, and grown out at temperature ranging from 14 to 16° C.

Color references are made to The Royal Horticultural Society Colour Chart (R.H.S.) 2001.

TABLE 1

DIFFERENCES BETWEEN THE NEW VARIETY 'ZOPFLAIR' AND A SIMILAR VARIETY

| | 'Zopflair' | 'Fiswipink' (U.S. Plant Pat. No. 16,686) |
|---|---|---|
| Flower color: | RHS N66C | RHS 58C |
| Inflorescences size: | Larger | Smaller |
| Petal quantity: | More petaloids | Fewer petaloids |
| Leaf zone: | Stronger | Weaker |
| Plant habit: | More upright/compact | Less upright/compact |

Plant:

*Form, growth and habit.*—Initially semi-upright, later creeping and trailing, medium sized, well-branched.

*Plant height.*—16.3 cm.

*Plant height (inflorescence included).*—About 22-26 cm.

*Plant width.*—19-20 cm.

*Garden performance and tolerance to weather.*—Very good.

*Crop time to flowering.*—About 10 weeks.

Roots:

*Number of days to initiate roots.*—15-18 days at about 22 degrees C.

*Number of days to produce a rooted cutting.*—21-23 days at 22 degrees C.

*Type.*—Fine, fibrous, free branching.

*Color.*—RHS N155B but whiter.

Foliage:

*Immature leaf, color upper surface.*—RHS 143A to RHS 143B.

*Immature leaf, lower surface.*—RHS 143B to RHS 143C.

*Mature leaf, color upper surface.*—RHS 137B to RHS 137C.

*Mature leaf, color lower surface.*—Between RHS 138A and RHS 143A.

*Length.*—4.5 cm.

*Width:* 7.3 cm.

*Shape.*—Ivy shaped with rounded lobes.

*Base shape.*—Cordate with gap between lowest lobes mostly closed.

*Apex shape.*—Rounded.

*Margin.*—Entire.

*Texture upper side.*—Pubescent.

*Texture lower side.*—Hirtellous, mostly along the edges and the veins.

*Leaf zonation color.*—Weak to medium distinctness RHS 166A.

*Leaf zonation diameter.*—About 3.2-3.5 cm.

*Color of veins, upper surface.*—Indistinct.

*Color of veins, lower surface.*—RHS 144A.

*Petiole color.*—RHS 143B to RHS 143C.

*Petiole length.*—4-5 cm.

*Diameter of petiole.*—0.2 cm.

*Texture.*—Finely pubescent.

Stem:

*Color of stem.*—RHS 143C, no anthocyanin.

*Length of stem.*—About 13-19 cm.

*Diameter.*—0.4 cm at middle part.

*Length of internodes.*—1-4 cm.

*Texture.*—Finely pubescent.

Inflorescence:

*Type.*—An umbel, semi-spherical or nearly semi-spherical, tight, medium sized composed of 7-10 flowers and buds.

*Blooming habit.*—Beginning of flowering with 50% of plants with open flowers: About mid-April, on about 11 week old plants.

*Lastingness of individual flowers.*—7-9 days at 18° C. temperature.

*Number of inflorescences per plant.*—4-7 when still in 12 cm pot, approx 13-18 in late summer.

*Fragrance.*—None.

*Umbel diameter.*—9-10 cm.

*Umbel depth.*—5.5-6.0 cm.

Peduncle:

*Color of peduncle.*—RHS 143A to RHS 143B.

*Length of peduncle.*—12-13 cm.

*Peduncle diameter.*—0.3 cm.

*Texture.*—Sparsely pubescent.

Pedicel:

*Color of pedicel.*—RHS 143A or RHS 146A, may be weakly infused with anthocyanin of about RHS 176B.

*Length of pedicel.*—3-3.1 cm.

*Diameter of pedicel.*—0.1 cm, often with a distinct 'joint' or 'spur'.

*Texture.*—Pubescent.

Bud (just before opening):

*Color.*—RHS 62D, often with deeper pink margins, RHS N66C to RHS 66D or even RHS 67C.

*Length.*—2.0-2.3 cm.

*Width.*—1.1-1.3 cm.

*Shape.*—Elliptical.

Corolla:

*Form.*—Polypetalous, somewhat overlapping.

*Number of petals.*—Approximately 15-18.

*Diameter of flower.*—5.5-6.0 cm.

*Depth of flower.*—1.7-2.0 cm.

*Color upper petals, upper surface.*—Between RHS N66C and RHSN66D, or RHS67D. At the base, veins of RHS 67B, and a small red dot, near RHS N57A.

*Color upper petals, lower surface.*—RHS 65A or lighter.

*Length of upper petals.*—3.2-3.4 cm.

*Width of upper petals.*—2.5-2.8 cm.

*Color lower petals, upper surface.*—RHS 68B or RHS 67D.

*Color lower petals, lower surface.*—RHS 65B, RHS 65C or RHS 65D.

*Length of lower petals.*—2.7-2.8 cm.

*Width of lower petals.*—1.9-2.1 cm.

*Petal shape.*—Mostly obovate, upper petals obovate to spathulate.

*Apex shape.*—Truncate or rounded.

*Margin.*—Entire.

*Base.*—Acute.

*Petal texture.*—Smooth, glabrous.

*Number of petaloids.*—0-3.

*Color of petaloids.*—Similar as petals, between RHS N66C and N66D or of somewhat less intense hue.

*Shape.*—Obovate, and often twisted or spiralling.

*Average width.*—Approximately 0.3-0.7 cm.

*Average length.*—Approximately 1.3-1.7 cm.

Calyx:

*Number of sepals.*—5.

*Color of sepals.*—RHS 143B to 143C abaxial; RHS 143C, largest sepal weakly RHS 182B adaxial.

*Length of sepals.*—1.1-1.4 cm.
*Width of sepals.*—0.5-0.6 cm for the largest sepal, 0.3 cm for the other sepals.
*Sepal shape.*—Lanceolate.
*Apex shape.*—Acute to acuminate.
*Margins.*—Entire.
*Texture.*—Villous.

Reproductive organs:

Gynoecium:
*Pistil.*—1.
*Length.*—0.9-1.1 cm.
*Style color.*—RHS 155D.
*Style length.*—0.4-0.5 cm.
*Stigma color.*—RHS 61B.
*Ovary color.*—RHS N138B.

Androecium:
*Number of anthers.*—2-5, occasionally 7.
*Length of anthers.*—0.2 cm.
*Anther color.*—RHS 72B.
*Length filaments.*—0.7-0.9 cm.
*Color of filaments.*—RHS 155D to RHS 68B, at upper end.
*Pollen amount.*—Moderate.
*Color of pollen.*—RHS 25A.

Fertility:
*Fruit development/seed set.*—Occasionally in late summer or early fall.
*Fruit.*—Oblong, about 0.9 cm in length and 0.4-0.5 cm in diameter, total length with rostrum (beak) is about 4.2 cm.
*Seed.*—Oblong, 0.4-0.5 cm long, 0.3 cm in diameter, brown.

Disease/pest resistance: Disease/pest resistance has not been observed on this hybrid.

What is claimed is:

1. A new and distinct variety of *Pelargonium* plant named 'Zopflair' substantially as illustrated and described herein.

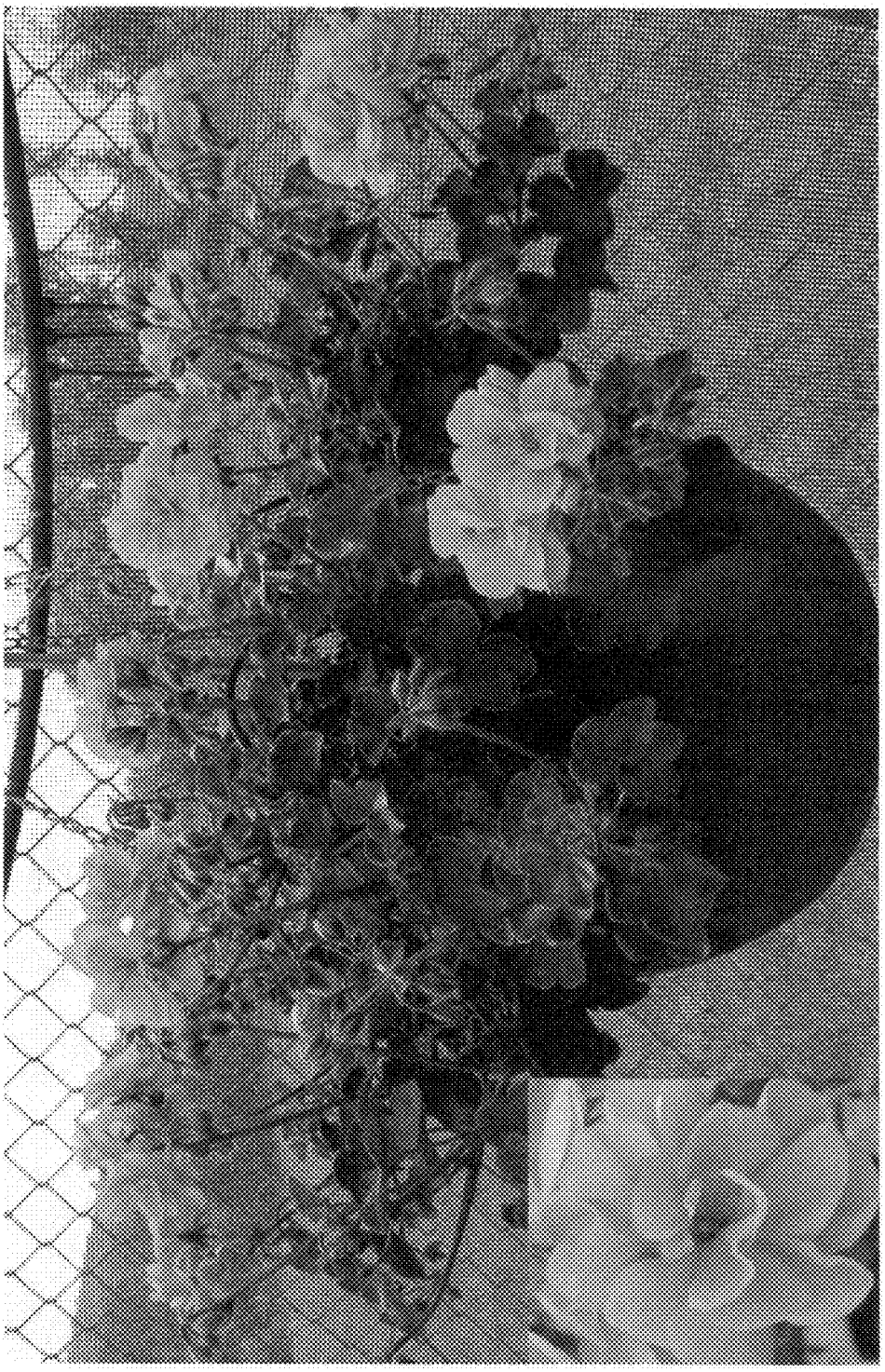

* * * * *